Figure 1:
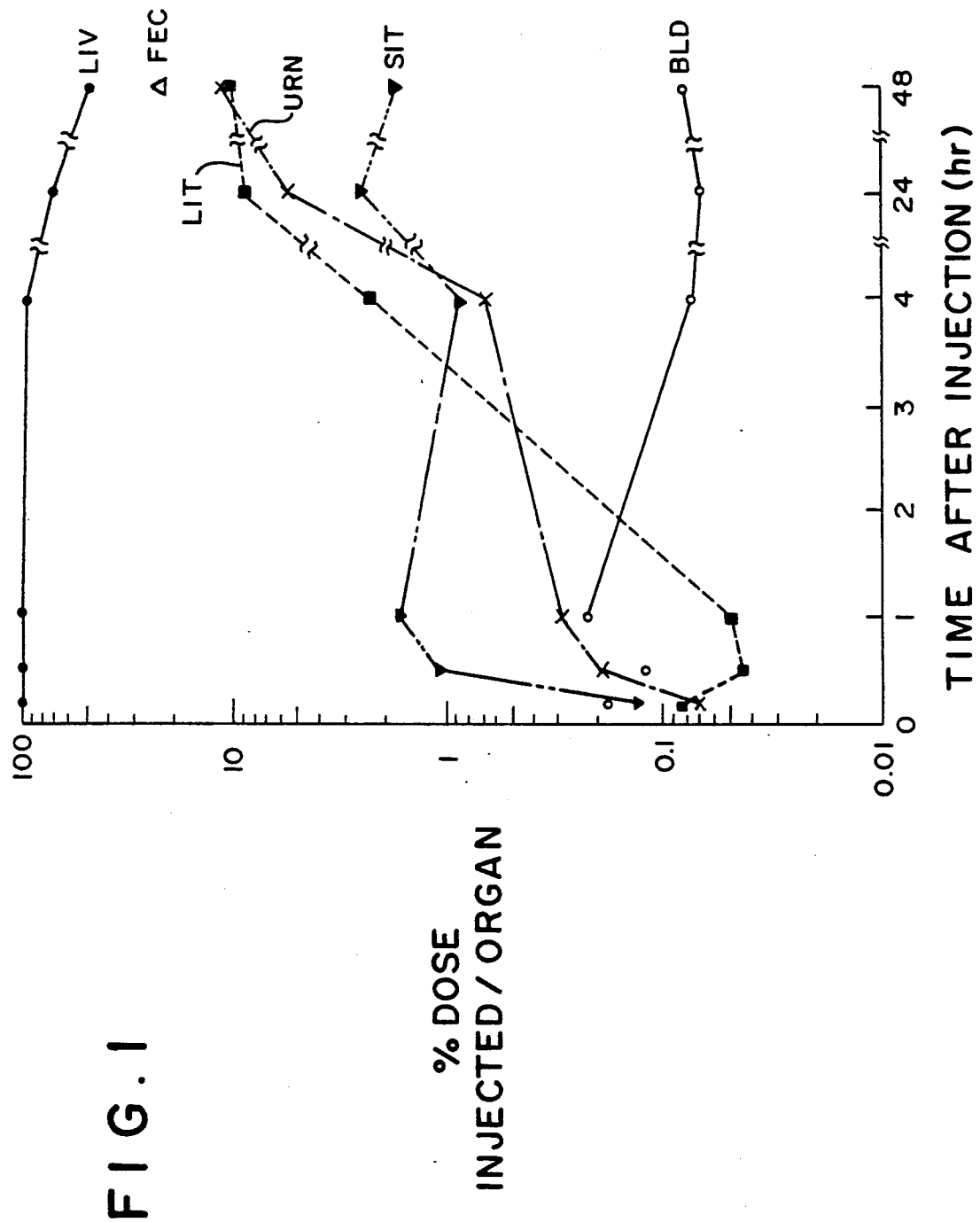

United States Patent [19]

Washino et al.

[11] Patent Number: 5,089,604
[45] Date of Patent: Feb. 18, 1992

[54] ASIALOGLYCOPROTEIN ACCEPTOR-DIRECTING COMPOUND HAVING CHELATEFORMING COMPOUND CHEMICALLY BONDED THERETO

[75] Inventors: Komei Washino; Miki Kurami; Nobuo Ueda, all of Chiba, Japan

[73] Assignee: Nihon Medi-Physics Co., Ltd., Hyogo, Japan

[21] Appl. No.: 423,212

[22] Filed: Oct. 18, 1989

Related U.S. Application Data

[62] Division of Ser. No. 139,558, Dec. 30, 1987, Pat. No. 5,032,678.

[30] Foreign Application Priority Data

Dec. 30, 1986 [JP] Japan .................. 61-312434
Dec. 30, 1986 [JP] Japan .................. 61-312435
Dec. 30, 1986 [JP] Japan .................. 61-312436

[51] Int. Cl.$^5$ .............................................. C07K 15/14
[52] U.S. Cl. .................................... 530/395; 530/350; 530/362; 530/363; 530/380; 530/402; 530/396; 424/1.1; 534/14
[58] Field of Search ............... 424/1.1; 530/362, 363, 530/402, 350, 380, 345, 300, 395; 534/14

[56] References Cited

U.S. PATENT DOCUMENTS

| | | | |
|---|---|---|---|
| 4,010,251 | 3/1977 | Green | 424/1.1 |
| 4,287,362 | 9/1981 | Yokoyama | 562/556 |
| 4,338,248 | 7/1982 | Yokoyama | 530/363 |
| 4,401,647 | 8/1983 | Krohn | 424/1.1 |
| 4,735,210 | 4/1988 | Goldenberg | 424/1.1 |

FOREIGN PATENT DOCUMENTS

| | | | |
|---|---|---|---|
| 24464 | 3/1981 | European Pat. Off. | |
| 233619 | 8/1987 | European Pat. Off. | 424/1.1 |
| 0308208 | 3/1989 | European Pat. Off. | |

OTHER PUBLICATIONS

Sundberg et al., J. Med. Chem., vol. 17, pp. 1304-1307 (1974).
Technetium in Chemistry and Nuclear Medicine 2, ed. by Nicolini, M. et al., article by Galli, G., et al., pp. 343-351 (11/86).
Vera, D. R., et al., J. Nucl. Med. 25: 779-787 (1984).
Vera, D. R., et al., Radiology, 151, 191-196 (1984).
Vera, D. R., et al., J. Nucl. Med. 26, 1157-1167 (1985).
Manabe, Y., et al., Biochimica et Biophysica Acta 883, 460-467 (1986).
Manabe, Y., et al., Chem. Abst. 105:222049y (1986).
van Rijk, P. P., et al., IRI Report 133-75-07, 1976, pp. 1-12.

*Primary Examiner*—F. T. Moezie
*Assistant Examiner*—Andrew G. Rozycki

[57] ABSTRACT

A high molecular compound useful as a non-radioactive carrier, which comprises at least one unit of (1) an asialoglycoprotein acceptor-directing compound and at least one unit of (2) a chelate-forming compound chemically bonded thereto, and which may be labeled with a radioactive metallic element to give a radioactive metallic element-labeled product useful as a radioactive diagnostic or therapeutic agent for liver.

2 Claims, 3 Drawing Sheets

ASIALOGLYCOPROTEIN ACCEPTOR-DIRECTING COMPOUND HAVING CHELATEFORMING COMPOUND CHEMICALLY BONDED THERETO

This is a divisional of co-pending application Ser. No. 07/139,558 filed on 12/30/87, now U.S. Pat. No. 5,032,678.

The present invention relates to a high molecular compound comprising a unit of an asialoglycoprotein acceptor-directing compound and a unit of a chelate-forming compound chemically bonded thereto, and its utilization. More particularly, it relates to a non-radioactive carrier for a radioactive metallic element which comprises a high molecular compound comprising a unit of an asialoglycoprotein acceptor-directing compound and a unit of a chelate-forming compound chemically bonded thereto, and a nuclear medicine such as a radioactive diagnostic or therapeutic agent prepared therefrom.

An asialoglycoprotein acceptor is a protein having a molecule-distinguishing ability and called "animal lectin". It is present widely in animal cells, particularly hepatic cells. An asialoglycoprotein acceptor isolated from human hepatic cells is constituted with a single polypeptide having a molecular weight of about 40,000 of and can recognize a glycoprotein having a galactose residue at the nonreductive terminal position of the saccharide chain (i.e. asialoglycoprotein).

While the physiological functions of an asialoglycoprotein acceptor are still uncertain, such acceptor as existing at the surfaces of hepatic cells is combined with a glycoprotein in the liver blood stream to form a complex, which is taken into and transported through the cells, during which it is dissociated in a lysosome. Thus, it is believed that an asialoglyroprotein acceptor would participate in the metabolism of a glycoprotein. In fact, the increase of the blood level of an asialoglycoprotein is observed in case of hepatic diseases such as chronic hepatitis, liver cirrhosis and hepatic cancer. Further, the decrease of the quantity of an asialoglycoprotein acceptor is observed in an experimental model of hepatic disorder induced by administration of chemicals. In view of these phenomena, it may be possible to diagnose hepatic diseases through assessment of the quantity and quality of an asialoglycoprotein acceptor determined by the use of an asialoglycoprotein-like substance, i.e. an asialoglycoprotein acceptor-directing compound.

In the field of nuclear medicine, there have been widely used physiologically active substances labeled with iodine-131 ($^{131}$I) such as $^{131}$I-labeled serum albumin, $^{131}$I-labeled fibrinogen and $^{131}$I-labeled tumor specific antibody for the purpose of imaging of specific organs, detection of physiological abnormalities, dynamic study of certain body systems, radiation therapy of tumors, etc. However, iodine-131 has a long half life of about 8 days and emits beta-rays so that the patient treated therewith is exposed to a large radiation dose. In addition, iodine-131 is apt to be deiodinated from physiologically active substances in living bodies so that normal organs may be damaged by radiation.

In order to overcome the above drawbacks in the $^{131}$I-labeled physiologically active substances, attempts have been made to provide radiopharmaceuticals comprising physiologically active substances and radioactive metallic elements having more favorable physical properties than iodine-131 combined thereto. Among such attempts, there is known a labeling method wherein a physiologically active substance is treated directly with a radioactive metal salt to make a chelate compound, which may be used as a radioactive diagnostic agent. For instance, human serum albumin is treated with an aqueous solution containing technetium-99 m ($^{99m}$Tc) in the form of pertechnetate in the presence of a reducing agent to give $^{99m}$Tc-labeled human serum albumin. Further, for instance, bleomycin is treated with an aqueous solution containing indium-111 ($^{111}$In) in the form of indium chloride to give $^{111}$In-labeled bleomycin. However, the chelate-forming property of those physiologically active substances is not sufficient, and the once formed chelating bond is readily broken. In fact, $^{99m}$Tc-labeled serum albumin and $^{111}$In-labeled bleomycin are low instability after administration into living bodies so that the behavior of the radioactivity in such bodies does not coincide with that of serum albumin or bleomycin as the physiologically active substance. This is a fatal defect for any nuclear medical diagnosis based on the exact trace of the behavior of the radioactivity which should coincide with the behavior of the physiologically active substance.

Attempts have been made to label an asialogalactoprotein acceptor-directing compound as a physiologically active substance with a radioactive metallic element such as technetium-99 m according to said conventional labeling procedure. For instance, neogalactoalbumin (galactose-combined serum albumin; NGA) was labeled with technedium-99 m through the residue of cysteine, lysine, glutamic acid or the like in its molecule. However, the labeling rate of the labeled product as well as the stability of such product in vitro and in vivo are not satisfactory. With the progress of the unstabilization, there are produced such impurities as colloidal technetium dioxide ($^{99m}$TcO$_2$). These impurities are taken into the reticuloendothelial system the liver so that correct assessment of the behavior of neogalactoalbumin becomes difficult or impossible. While the stability is surely enhanced by the use of a larger amount of a stannous salt as a reducing agent on the labeling, the stannous salt is apt to make a colloidal substance at an acidic pH region under which labeling is effected, and such colloidal substance makes precise imaging difficult. The use of neogalactoalbumin in an excessive amount is effective to combine free stannous salt thereto so that the precise imaging may be made possible, but in such case, a radioactivity concentration becomes lower.

As a result of an extensive study, it has been found that a high molecular compound comprising a unit of an asialoglycoprotein acceptor-directing compound and a unit of a chelate-forming compound chemically bonded thereto is useful as a non-radioactive carrier for a radioactive metallic element. A radioactive metallic element-labeled high molecular compound obtained by labeling said high molecular compound with a radioactive metallic element shows a high radioactivity with a high stability in vitro and in vivo. Therefore, it can assure a satisfactory diagnosis or therapy by the use in a relatively small amount. Thus, said labeled product is useful as a nuclear medicine such as a radioactive diagnostic or therepeutic agent, particularly the liver. Quite advantageously, this technique is widely applicable to asialoglycoprotein acceptor-directing compounds, i.e. not only those having a structure capable of bonding a radioactive metallic element directly thereto (e.g. neogalactoalbumin) but also those not having said structure in themselves.

According to the present invention, there is provided (A) a high molecular compound useful as a non-radioactive carrier for a radioactive metallic element, which comprises a unit of (1) an asialoglycoprotein acceptor-directing compound and a unit of (2) a chelate-forming compound chemically bonded thereto as well as (B) a radioactive metallic element-labeled high molecular compound useful as a radioactive diagnostic or therapeutic agent, which comprises said high molecular compound (B) and (3) a radioactive metallic element chelate-bonded thereto.

The asialoglycoprotein acceptor-directing compound (1) is a compound having a binding affinity to an asialoglycoprotein acceptor in a living body, of which a typical example is neogalactoalbumin. Neogalactoalbumin can be separated from natural sources and also synthesized from serum albumin and galactose, both being obtainable commercially in highly pure states. Other examples are asialoglycoproteins (e.g. asialoorosomucoid, asialofetuin, asialoceluloplasmin, asialohaptoglobin), galactose-bonded polylysine, galactose-bonded polyglucosamine, etc.

As the chelate-forming compound (2), there may be used any one which has a functional group (e.g. amino, carboxyl, formyl, mercapto) capable of reacting with the asialoglycoprotein acceptor-directing compound (1) under relatively mild conditions and a structure capable of forming a strong chelate bond with a radioactive metallic element (3). The one which has a bifunctional moiety capable of combining with a radioactive metallic element through a chelate bond is especially favorable. Specific examples are deferoxamine, diethylenetriaminepentaacetic acid of the formula:

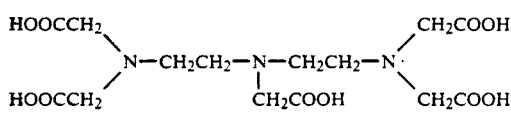

and its cyclic anhydride, ethylenediaminetetraacetic acid succinimide ester of the formula:

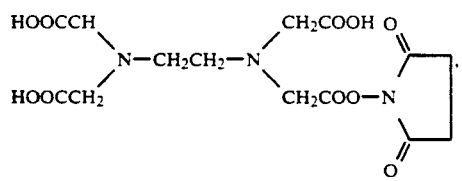

2-propionaldehyde-bis(thiosemicarbazone) derivatives of the formula:

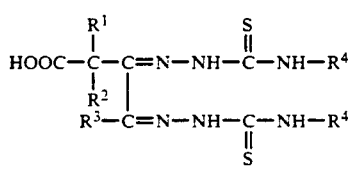

wherein $R^1$, $R^2$, $R^3$ and $R^4$ are each a hydrogen atom or a $C_1$-$C_3$ alkyl group, 3-aminomethylene-2,4-pentadione-bis(thiosemicarbazone) derivatives of the formula:

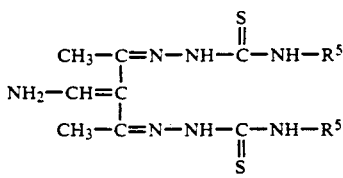

wherein $R^5$ is a hydrogen atom, a $C_1$-$C_3$ alkyl group or a phenyl group, 1-(p-aminoalkyl)phenylpropane-1,2-dione-bis(thiosemicarbazone) derivatives of the formula:

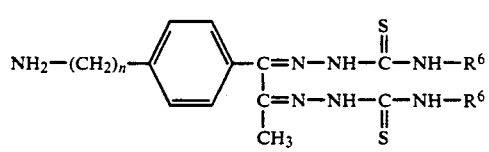

wherein $R^6$ is a hydrogen atom or a $C_1$-$C_3$ alkyl group and n is an integer of 0 to 3, etc.

Even such a compound as having a metal capturing property to form a chelate but not a functional group capable of reacting with the asialoglycoprotein acceptor-directing compound (1) under mild condition may be used as the chelate-forming compound (2) after modification for introduction of said functional group therein. Examples of such compound include dimercaptoacetylethylenediamine, bisadminoethanethiol, N,N'-bis(2-hydroxyethyl)ethylenediamine, etc.

The above chelate-forming compounds (2) are all of relatively low molecular weight and have only a single chelate forming structure; namely, they are "lower" molecular weight compounds. When the asialoglycoprotein acceptor-directing compound (1) has many functional groups reactive to the chelate-forming compound (2), the high molecular compound (A) as obtained can also have many units of the chelate-forming compound (2) so that a sufficiently high radioactivity concentration as necessitated for diagnosis or therapy will be usually retained. When, however, the asialoglycoprotein acceptor-directing compound (1) has only a single or few functional groups, the high molecular compound (A) can also have only a single or few units of the chelate-forming compound (2) so that a the high radioactivity concentration required for diagnosis or therapy may be hardly maintained. In order to overcome this drawback, the chelate-forming compound (2) may be constructed from a polymeric compound having a number of functional groups and a number of said chelate-forming compound of lower molecular weight chemically bonded thereto, whereby the resulting high molecular compound (A) can retain a high radioactivity concentration. In this case, the chelate-forming compounds (2) are of relatively high molecular weight and have a number of chelate forming to structures namely. they are "higher" molecular weight compounds.

Examples of said polymeric compound having a number of functional groups usable for production of the chelate-forming compound (2) of higher molecular weight are polysaccharides such as pentosanes, hexosanes, polyglycosamines, polyuronic acids, glucosaminoglycanes, glycouronoglycanes and heterohexosamines. More specifically, there are exemplified amylose, amylopectin, dextrane, cellulose, inulin, pectinic acid, prurane derivatives, etc. Other examples are polyacrolein derivatives, polysuccinimide derivatives, polyamine derivatives, polylysinepolyimine derivatives, etc.

For production of the high molecular compound (A), the asialoglycoprotein acceptor-directing compound (1) and the chelate-forming compound (2) may be subjected to chemical reaction directly or through a crosslinking agent by a per se conventional procedure, followed by purification (e.g. dialysis, salting out, gel filtration, ion exchange chromatography, electrophoresis) in a per se conventional manner. The number of the molecules of the chelate-forming compound (2) to be combined to one molecule of the asialoglycoprotein acceptor-directing compound (1) is not limitative insofar as the physiological property of the latter is substantially kept. It is usually preferred to be 30 or less. Particularly, when the chelate-forming compound (2) is a higher molecular weight compound as explained above, the number of the molecules of the chelate-forming compound (2) may be 10 or less per one molecule of the asialoglycoprotein acceptor-directing compound (1).

Alternatively, the high molecular compound (A) may be produced by reacting a portion of the asialoglycoprotein acceptor-directing compound (1) with the chelate-forming compound (2) optionally in the presence of a crosslinking agent and then reacting the resultant product with the remaining portion of the asialoglycoprotein acceptor-directing compound (1).

Taking neogalactoalbumin as an example of the asialoglycoprotein acceptor-directing compound (1) and diethylenetriaminepentaacetic acid cyclic anhydride as an example of the chelate-forming compound (2), a typical procedure for preparation of a neogalactoalbumin (NCA)-diethylenetriaminepentaacetic acid (DTPA) combined product as the high molecular compound (A) will be hereinafter explained in detail.

To human serum albumin (HSA; a commercially available injectionable preparation of human serum albumin preparation), phosphate buffer and DTPA cyclic anhydride are added, followed by stirring at room temperature for several minutes. Borate buffer is added thereto for adjustment of pH to give a solution of an HSA-DTPA combined product. Separately, a methanolic solution of sodium methoxide is added to cyanomethyl-thiogalactose, followed by stirring at room temperature for about several 10 hours. Evaporation of the methanol gives 2-iminomethoxy-1-thiogalactose. The above prepared HSA-DTPA solution is added thereto, followed by allowing to stand at room temperature for 24 hours. Acetic acid is added thereto for interruption of the reaction, and pH is adjusted to give a solution of an NGA-DTPA combined product. The thus prepared NGA-DTPA combined product is considered to have the following chemical structure:

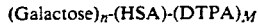
(Galactose)$_n$-(HSA)-(DTPA)$_M$ wherein m and n indicate each an integer of 1 to 50 but m+n is an integer of 2 to 50. NGA The thus obtained high molecular compound (A) is useful as a non-radioactive carrier for a radioactive metallic element and may be labeled with any appropriate radioactive metallic element to give a radioactive metallic element-labeled high molecular compound (B), which is per se useful as a radioactive diagnostic or therapeutic agent. Namely, the high molecular compound (A) has a chelate-forming structure originated from the chelate-forming compound (2), and such structure can capture firmly a radioactive metallic element (3) by a chelate bond. Therefore. even such an asialoglycoprotein acceptor-directing compound (1) as has itself been not labeled with a radioactive metallic element can be well labeled to give a stable labeled product.

The radioactive metallic element (3) covers any metallic element having radioactivity, which has physical and/or chemical characteristics suitable for nuclear medical diagnosis or therapy and can be readily captured with the chelate-forming structure in the chelate-forming compound (2). Specific examples of a radioactive metallic element for a diagnostic purpose are gallium-67 ($^{67}$Ga), gallium-68 ($^{68}$Ga), thallium-201 ($^{201}$Tl), indium-111 ($^{111}$In), technethium-99m ($^{99m}$Tc), copper-62 ($^{62}$Cu), etc. Specific examples of a radioactive metallic element for a therapeutic purpose are yttrium-90 ($^{90}$Y), palladium-109 ($^{109}$Pd), rhenium-186 ($^{186}$Re), gold-198 ($^{198}$Au), bismuth-212 ($^{212}$Bi), etc. They are normally employed in their salt forms, particularly in their water-soluble salt forms.

Depending upon the kind or state of the radioactive metallic element (3), two different labeling procedures may be adopted. When the radioactive metallic element (3) is in a valency state which can form a stable chelate compound, the high molecular compound (A) may be contacted with the radioactive metallic element (3) in an aqueous medium to form the radioactive metallic element-labeled high molecular compound (B). This labeling manner may be applied to $^{67}$Ga, $^{111}$In, etc. When the radioactive metallic element (3) is in a valency state which has to be changed for the formation of a stable chelate compound, the high molecular compound (A) may be contacted with the radioactive metallic element (3) in an aqueous medium in the presence of a reducing agent or an oxidizing agent to form the radioactive metallic element-labeled high molecular compound (B). This labeling manner may be applied to $^{99m}$Tc, etc.

Examples of the reducing agent are stannous salts, i.e. salts of divalent tin ion (Sn++). Specific examples are stannous halides (e.g. stannous chloride, stannous fluoride), stannous sulfate, stannous nitrate, stannous acetate, stannous citrate, etc. Sn++ ion-bearing resins, e.g. ion-exchange resins charged with Sn++ ion, are also suitable. Examples of the oxidizing agent are hydrogen peroxide, etc.

When, for example, the radioactive metallic element (3) is $^{99m}$Tc, the high molecular compound (A) may be treated with $^{99m}$Tc in the form of a pertechnetate in an aqueous medium in the presence of a reducing agent, e.g. a stannous salt. There is no particular requirement concerning the order of the introduction of the above reagents into the reaction system. Usually, however, initial mixing of the stannous salt with the pertechnetate in an aqueous medium should be avoided. The stannous salt may be used in an amount that can sufficiently reduce the pertechnetate.

The high molecular compound (A) and the radioactive metallic element-labeled high molecular compound (B) above obtained are useful as a non-radioactive carrier and as a radioactive diagnostic or therapeutic agent, respectively. They are sufficiently stable and therefore may be stored as such and supplied on demand. In the most practical manner, the high molecular compound (A) is stored as such or in the form of an aqueous solution or a lyophilized powder and, on the use, combined with the radioactive metallic element (3) in an aqueous medium to make the radioactive metallic element-labeled high molecular compound (B). When desired, the non-radioactive carrier as well as the radioactive diagnostic or therapeutic agent may contain any suitable additive such as a pH controlling agent (e.g. an acid, a base, a buffer), a stabilizer (e.g. ascorbic acid) or an isotonizing agent (e.g. sodium chloride) in addition to said major component.

The radioactive metallic element-labeled high molecular compound (B) is useful for nuclear medical diagnosis or therapy, particularly in liver. For such purpose, the radioactive metallic element-labeled high molecular compound (B) is usually administered to living bodies such as human bodies through an intravenous route in an amount sufficient to produce radioactivity effective for the diagnostic or therapeutic purpose. However, any other route which is advantageous for exhibition of its physical activity may be adopted. For instance, the intravenous administration of a $^{99m}$Tc-labeled product in an amount of about 0.5 to 5 ml, particularly about 1 to 3 ml, having a radioactivity of about 0.1 to 50 mCi, particularly about 1 to 20 mCi, to a patient is quite suitable for diagnostic purpose.

The advantages of the high molecular compound (A) of this invention, which is useful as a non-radioactive carrier, may be summarized as follows: (a) it is stable over a long period of time after manufacture; (b) since it can be produced under mild conditions, no unfavorable side reactions such as inactivation, denaturation or decomposition are caused; (c) any asialoglycoprotein acceptor-directing compound can be used as the starting material; (d) the radioactive metallic element-labeled high molecular compound (B) can be formed by a very simple procedure, e.g. by merely contacting with a radioactive metallic element in an aqueous medium. The advantages of the radioactive metallic element-labeled high molecular compound (B) useful as a radioactive diagnostic agent may be also summarized as follows: (a) it is stable over a long period of time after manufacture; (b) the labeling efficiency with the radioactive metallic element is extremely high; (c) since the labeling operation is quite simple, no unfavorable side reactions such as inactivation, denaturation or decomposition are caused; (d) among various radioactive metallic elements, the most suitable one for the diagnostic or therapuetic purpose may be chosen; (e) high and stable radioactivity can be obtained in a relatively small amount.

The radioactive metallic element-labeled high molecular compound (B) is particularly useful as a diagnostic agent for imaging of an organ or tissue having an asialoglycoprotein acceptor, detection of a disease producing any modification of the quantity and/or quality of an asialoglycoprotein acceptor and dynamic examination of an asialoglycoprotein acceptor. When, for instance, it comprises $^{99m}$Tc as the radioactive metallic element (3) and is used as a liver-imaging agent, $^{99m}$Tc is firmly bonded through a chelate-bond so that it is accumulated in liver in a stable state for a properly long time, during which specto-imaging photography can be readily carried out. Yet, the radioactivity is excreted from a human body so quickly as not affording any unfavorable influence on the human body and not preventing the purpose of diagnosis. In addition, it is advantageous that the toxicity and the antigenicity are sufficiently low.

Practical and presently preferred embodiments of the invention are illustratively shown in the following Examples wherein % is by weight unless otherwise indicated.

EXAMPLE 1

Preparation of a non-radioactive carrier comprising a neogalactoalbumin-diethylenetriaminepenta-acetic acid combined product:

To 20% human serum albumin (HSA) solution (50 ml), 0.1N phosphate buffer (pH, 8.0; 117 ml) was added, and diethylenetriaminepentaacetic acid cyclic anhydride (521 mg) was added thereto while stirring by the aid of a magnetic stirrer at 4° C. for about 5 minutes. To the resultant mixture, 1N sodium hydroxide solution (10 ml) and 0.6M borate buffer (pH, 8.5; 23 ml) were added to give a HSA-DTPA solution.

To 0.05 ml of the resulting mixture, 0.1M citrate buffer (0.1 ml) was added, and 0.1 ml of the resultant mixture was added to a vial where 1 mM indium chloride (0.3 ml), indium chloride ($^{111}$In) (2 mCi/ml; 0.4 ml) and 0.1M citrate buffer (0.6 ml) were previously charged, followed by allowing to stand at room temperature for 30 minutes. To the resulting mixture, 1 mM diethylenetriaminepentaaceitic acid (DTPA) solution (0.3 ml) was added, and HSA-DTPA-$^{111}$In and free $^{111}$In-DTPA were separated by electrophoresis under the following conditions, and their radioactivities were determined:

Support: cellulose acetate membrane;
Buffer: 0.06M Barbital buffer (pH, 8.6);
Conditions: 1 mA/cm, 30 minutes.

The result as obtained was calculated according to the following formula to obtain the binding ratio (P) of DTPA per one molecule of HSA:

$$P = 0.2055 \times A/W$$

wherein W is the amount (mg) of HSA added to the vial and A is the percentage (%) of $^{111}$In-labeled HSA-DTPA. The binding ratio was about 5.

Separately, cyanomethyl-thiogalactose (10 g) was dissolved in dry methanol (250 ml) at 50° C., and sodium methoxide (270 mg) was added thereto, followed by stirring at room temperature for 48 hours. After evaporation of the methanol under reduced pressure, the concentrated product was added to the HSA-DTPA solution, and the resultant mixture was allowed to stand at 4° C. overnight to give an NGA-DTPA combined product, which was purified by high performance liquid chromatography under the following conditions:

Column: TSK-3000SW column (5.1 cm × 60 cm);
Eluting solution: 0.1M sodium chloride solution;
Eluting speed: 20 ml/min.

All the above operations other than measurement of the binding rate were carried out aseptically. All reaction vessels and instruments were previously subjected to heat treatment at 180° C. for 4 hours, or subjected to washing with injectionable distilled water and sterilization in an autoclave. The buffer was prepared using injectionable distilled water and filtered through a membrane filter for sterilization. The column was washed with sodium hypochlorite solution and then equilibrated with 0.1M sodium chloride solution.

The thus obtained NGA-DTPA combined product was diluted with 0.1M citrate buffer to make a concentration of 1 mg/ml. The diluted solution was filtered through a membrane filter and charged into vials in an amount of 1 ml per vial to give a non-radioactive carrier containing an NGA-DTPA combined product.

EXAMPLE 2

Preparation of a radioactive diagnostic agent comprising a $^{111}$In-labeled NGA-DTPA combined product:

To the vial containing the NGA-DTPA combined product as obtained in Example 1, an injectionable solution of indium ($^{111}$In) chloride (2 mCi/ml; 1.0 ml) was added to make a radioactive diagnostic agent comprising a $^{111}$In-labeled NGA-DTPA combined product.

Analysis was carried out on 25 ul of the above radioactive diagnostic agent according to high performance liquid chromatography under the following condition, whereby it was confirmed that the dimer is present in an amount of 1% and unreacted DTPA is not detected:

Column: TSK-3000SW manufactured by Toyo Soda (0.75 × 60 cm);
Eluting solution: 0.1M sodium chloride solution;
Eluting speed: 0.75 ml/min.

The major component showed a retention time of about 25 minutes, and its average molecular weight as calculated from the calibration curve was about 75,000.

Figure 2:
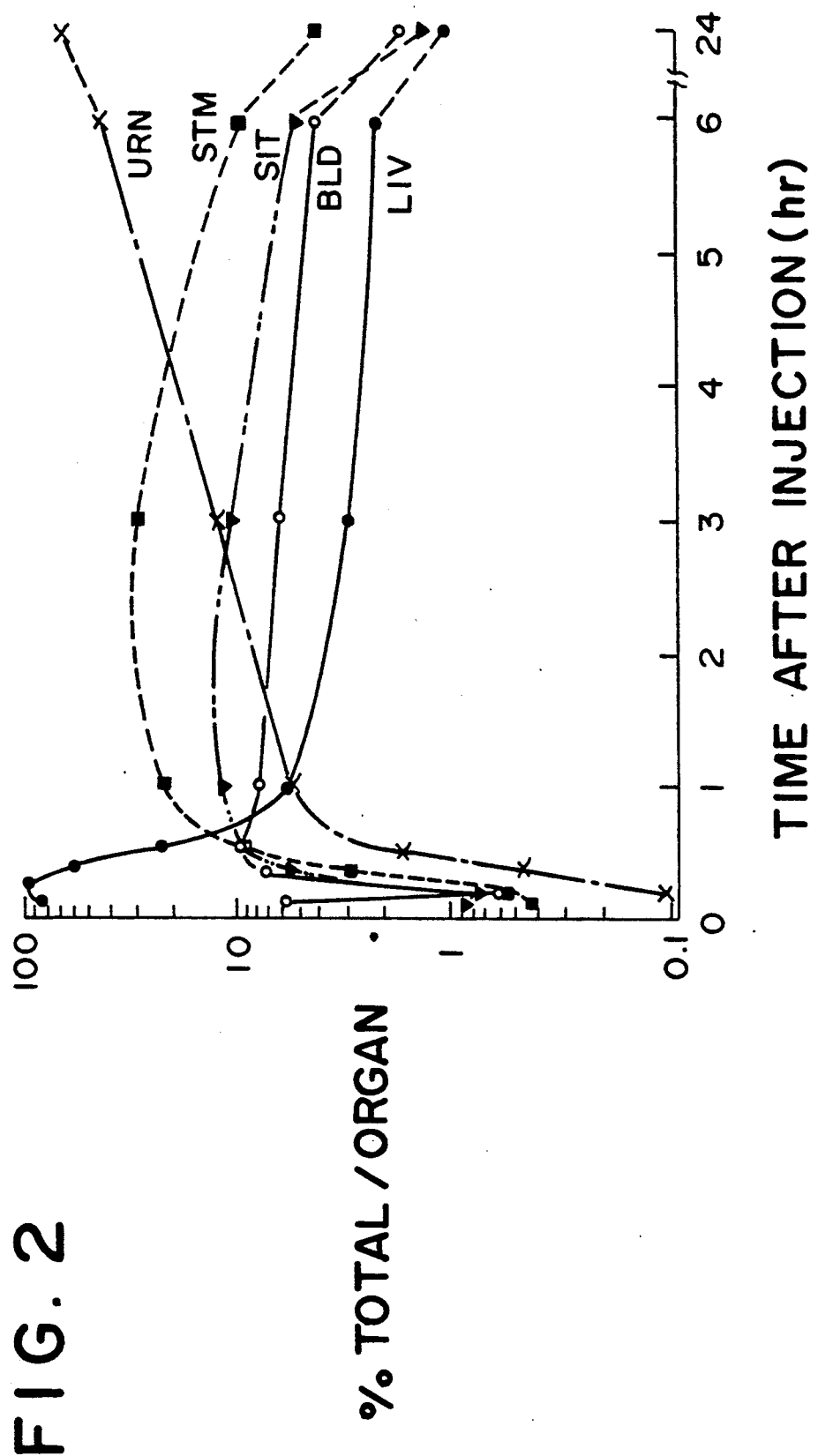

The above prepared radioactive diagnostic agent comprising an $^{111}$In-labeled NGA-DTPA combined product (380 ug) was administered intravenously to an SD strain female rat, and the distribution behavior in the animal body with the lapse of time after the administration was observed. The results are shown in FIG. 1 of the accompanying drawings (wherein LIV: liver; FEC: feces; LIT: large intestine; URN: urine; SIT: small intestine; BLD: blood; STM: stomach), while the results with $^{123}$I-labeled NGA as control are shown in FIG. 2. As understood from the comparison, $^{123}$I-combined NGA is taken into liver through an asialoglycoprotein acceptor and deiodinated therein to give free iodine, which is accumulated in stomach or excreted quickly into urine. On the other hand, $^{111}$In-labeled NGA-DTPA is excreted mainly into intestinal canal from liver and metabolized through an asialoglycoprotein acceptor.

EXAMPLE 3

Preparation of a non-radioactive carrier comprising an NGA-DTPA(Sn) combined product:

The NGA-DTPA combined product as obtained in Example 1 was diluted with physiological saline to make a concentration of 15 mg/ml. To the dilute solution, stannous chloride (0.4 mM) and ascorbic acid (1.5 mM) were added, and the pH was adjusted with aqueous hydrochloric acid within a range of 3 to 5. The resulting solution was filtered through a membrane filter and charged into vials in an amount of 1 ml per vial to give a non-radioactive carrier containing an NGA-DTPA(Sn) combined product.

EXAMPLE 4

Preparation of a radioactive diagnostic agent comprising a $^{99m}$Tc-labeled NGA-DTPA combined product:

To the vial containing the NGA-DTPA(Sn) combined product as obtained in Example 3, an injectionable solution of sodium pertechnetate (50 mCi/ml; 1 ml) was added to give a radioactive diagnostic agent comprising a $^{99m}$Tc-labeled NGA-DTPA combined product.

Figure 3:
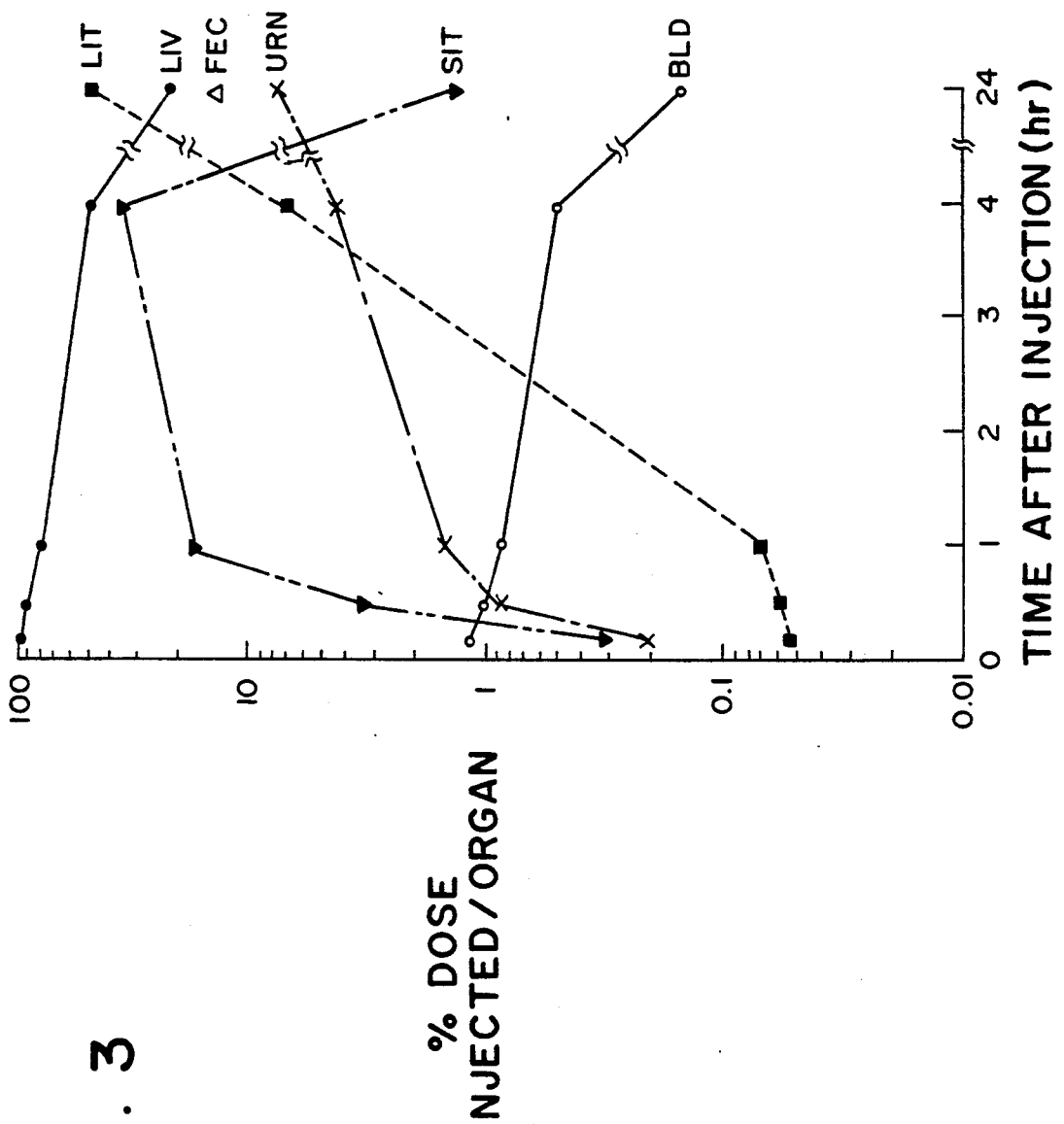

The distribution behavior of said labeled product in female rat was examined as in Example 2. The results are shown in FIG. 3 of the accompanying drawings. As understood from the resultas as shown therein, the labeled product is quickly taken into liver and excreted mainly through intestinal canal; the behavior in the animal body is stable.

Also, electrophoresis was carried out on the labeled product as in Example 1 for measurement of the labeling rates 1 hour, 4 hours and 24 hours after labeling. The results are shown in Table 1, from which it is understood that $^{99m}$Tc-labeled NGA-DTPA clearly is more stable and gives higher labeling rate than $^{99m}$Tc-labeled NGA.

TABLE 1

| Labeled product | Labeling rate (%) Time lapsed after labeling (Hrs) | | |
|---|---|---|---|
| | 1 | 4 | 24 |
| $^{99m}$Tc-labeled NGA-DTPA | 81 | 94 | 94 |
| $^{99m}$Tc-labeled NGA | 74 | 77 | 77 |

EXAMPLE 5

Preparation of a non-radioactive carrier composition comprising an NGA-Amylose (Amyl)-deferoxamine (DFO) combined product:

Deferoxamine (DFO) (15 mg) was dissolved in 0.03M phosphate buffer (pH 7.0) (1 ml), and triethylamine (3.2 ul) was added thereto, followed by stirring at room temperature. An aqueous solution of dialdehydoamylose (25 mg/ml; 1 ml) was added thereto, and the resultant mixture was stirred at room temperature for 30 minutes to give a solution (A).

Separately, cyanomethyl-thiogalactose (1 g) was dissolved in dry methanol (25 ml) at 50° C., and sodium methoxide (27 mg) was added thereto, followed by stirring at room temperature for 48 hours. After evaporation of methanol under reduced pressure, 0.2M borate buffer (20 ml) containing HSA (1 g) was added thereto, and the reaction was effected at 4° C. overnight to give an NGA solution as a solution (B).

The solution (A) (2 ml) and the solution (B) (2 ml) were combined together, and the resultant mixture was stirred at room temperature for about 6 hours. Hydrated sodium borate (1.5 mg) was added thereto, followed by stirring at room temperature for about 1 hour for reduction. The reaction mixture was dialyzed against 1M sodium chloride solution and then subjected to column chromatography on Sephacryl S-200 (diameter, 2.2 cm; length, 50 cm) using 0.03M phosphate buffer (pH 7.0) as an eluting solvent for purification of the produced NGA-Amyl-DFO combined product.

The thus obtained NGA-Amyl-DFO combined product was diluted with 0.03M phosphate buffer to make a concentration of 1 mg/ml. The diluted solution was filtered through a membrane filter and charged into vials in an amount of 1 ml per vial to give a non-radioactive carrier comprising an NGA-Amyl-DFO combined product.

The amounts of amylose and DFO in said combined product were analyzed by electrophoresis. Namely, a portion of the reaction mixture after the above reduction was admixed with an injectionable solution of gallium ($^{67}$Ga) citrate (2 mCi) for labeling. Based on the amounts of $^{67}$Ga-labeled NGA-Amyl-DFO, $^{67}$Ga-labeled Amyl-DFO and $^{67}$Ga-labeled DFO as determined by electrophoresis, the numbers of the DFO molecule and the amylose molecule in said combined product were respectively calculated to be 11.5 and 0.7 per one molecule of NGA.

EXAMPLE 6

Preparation of a radioactive diagnostic composition comprising a $^{67}$Ga-labeled NGA-Amyl-DFO combined product:

To a vial containing an NGA-Amyl-DFO combined product, an injectionable gallium ($^{67}$Ga) citrate solution (2 mCi) was added to give a radioactive diagnostic agent comprising a $^{67}$Ga-labeled NGA-Amyl-DFO combined product. The operation was carried out aseptically. The labeled product was confirmed by electrophoresis to be of high purity.

EXAMPLE 7

Preparation of a non-radioactive carrier comprising a polylysine (PolyLys)-DTPA-galactose (Gal) combined product:

Polylysine hydrobromide (average molecular weight, about 8,000) (77 mg) was dissolved in 0.2M borate buffer (pH, 8.5; 2 ml), and diethylenetriaminepentaacetic acid cyclic anhydride (25 mg) was added thereto while stirring. The resultant mixture was stirred at room temperature for 5 minutes. An appropriate amount of 2N sodium hydroxide solution and 0.2M borate buffer (pH, 8.5; 1 ml) were added to make a PolyLys-DTPA combined product.

To 0.1 ml of the above obtained PolyLys-DTPA product, 0.1M citrate buffer (0.2 ml) and indium ($^{111}$In) chloride solution (2 mCi/ml; 0.1 ml) were added, and the resultant mixture was allowed to stand for 30 minutes for labeling. The labeled product was analyzed by electrophoresis to determine the amounts of $^{111}$In-labeled PolyLys-DTPA and $^{111}$In-labeled DTPA, from which the number of DTPA molecule combined to one molecule of PolyLys was calculated to be about 3.

Separately, cyanomethyl-thiogalactose (2 g) was added to a mixture of methanol (50 ml) and sodium methoxide (54 mg), and stirring was continued at room temperature for 48 hours. After evaporation of methanol under reduced pressure, a total amount of the above prepared PolyLys-DTPA combined product was added thereto, and stirring was continued at 35° to 40° C. for 1.5 hours to give a PolyLys-DTPA-Gal combined product (wherein DTPA and Gal are respectively combined to PolyLys), which was purified by gel filtration chromatography under the following conditions:

Gel: Cellophaine GC-25 m (column, 2.2 cm × 50 cm);
Eluting solution: 0.1M citrate buffer (pH, 5.7).

The thus obtained PolyLys-DTPA-Gal combined product was diluted with 0.1M citrate buffer (pH, 5.7) to make a concentration of 1 mg/ml. The diluted solution was filtered through a membrane filter and charged into vials in an amount of 1 ml per vial to give a non-radioactive carrier.

EXAMPLE 8

Preparation of a radioactive diagnostic agent comprising a $^{111}$In-labeled PolyLys-DTPA-Gal combined product:

An injectionable indium ($^{111}$In) chloride solution (2 mCi; 1.0 ml) was added to a vial containing PolyLys-DTPA-Gal combined product as prepared in Example 7 to make an injectionable composition comprising a $^{111}$In-labeled PolyLys-DTPA-GAL combined product useful as a radioactive diagnostic agent.

The injectionable composition was intravenously administered to a female rat (SD strain; bodyweight, 380 ug) through tail vein for examination of the distribution behavior of the $^{111}$In-labeled PolyLys-DTPA-Gal product in the animal. The results are shown in Table 2, from which it is understood that said labeled product is quickly taken up into liver through the asialoglycoprotein acceptor therein and then gradually excreted. Thus, it is useful for assessment of the asialoglycoprotein acceptor.

TABLE 2

| Organ | Percent to the amount administered | | |
|---|---|---|---|
| | After 10 minutes | After 30 minutes | After 1 hour |
| Liver | 52.80 | 72.33 | 60.60 |
| Spleen | 0.57 | 0.52 | 0.52 |
| Stomach | 0.37 | 0.35 | 0.25 |
| Small intestine | 1.58 | 3.31 | 3.31 |
| Large intestine | 1.14 | 0.43 | 0.63 |
| Lung | 0.52 | 0.31 | 0.37 |
| Heart | 0.19 | 0.41 | 0.14 |
| Kidney | 7.99 | 4.06 | 5.75 |
| Blood | 3.35 | 1.10 | 1.55 |
| Bone | 29.30 | 10.68 | 13.00 |
| Urine | 2.20 | 6.76 | 13.87 |

What is claimed is:

1. A compound useful as a carrier for a radioactive metallic element, which consists of at least one unit of (1) an asialoglycoprotein acceptor-directing compound selected from the group consisting of neogalactoalbumin, asialooromucoid, asialofetuin, asialoceluloplasmin, asialohaptoglobin, galactose-bonded polylysine and galactose-bonded polyglycosamine, and at least one unit of (2) diethylenetriaminepentaacetic acid chemically bonded thereto.

2. The compound according to claim 1, wherein the asialoglycoprotein acceptor-directing compound is neogalactoalbumin.

* * * * *